United States Patent
Verma et al.

(10) Patent No.: US 11,800,968 B2
(45) Date of Patent: *Oct. 31, 2023

(54) METHOD FOR ADJUSTING AN EXPOSURE OF AN ENDOSCOPE

(71) Applicant: Verily Life Sciences LLC, South San Francisco, CA (US)

(72) Inventors: Nishant Verma, Burlingame, CA (US); Ryan L Robertson, Sunnyvale, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/059,087

(22) Filed: Nov. 28, 2022

(65) Prior Publication Data

US 2023/0092807 A1 Mar. 23, 2023

Related U.S. Application Data

(63) Continuation of application No. 17/123,650, filed on Dec. 16, 2020, now Pat. No. 11,576,554.

(60) Provisional application No. 62/951,716, filed on Dec. 20, 2019.

(51) Int. Cl.
| | |
|---|---|
| *A61B 1/07* | (2006.01) |
| *A61B 1/00* | (2006.01) |
| *A61B 1/06* | (2006.01) |
| *H04N 23/71* | (2023.01) |

(Continued)

(52) U.S. Cl.
CPC ...... *A61B 1/00006* (2013.01); *A61B 1/00009* (2013.01); *A61B 1/00045* (2013.01); *A61B 1/0655* (2022.02); *A61B 1/07* (2013.01); *H04N 23/71* (2023.01); *H04N 23/72* (2023.01); *H04N 23/555* (2023.01)

(58) Field of Classification Search
None
See application file for complete search history.

(56) References Cited

U.S. PATENT DOCUMENTS

| | | |
|---|---|---|
| 5,475,420 A | 12/1995 | Buchin |
| 8,626,272 B2 | 1/2014 | Avni et al. |
| 8,712,151 B2 | 4/2014 | Zhao et al. |

(Continued)

*Primary Examiner* — Samuel D Fereja
(74) *Attorney, Agent, or Firm* — Christensen O'Connor Johnson Kindness, PLLC

(57) ABSTRACT

Methods, endoscopic systems, and non-transitory, machine-readable storage media for adjusting an exposure of an endoscopic system are described. In an embodiment, the methods include emitting light with a light source into a proximal end of an endoscope light pipe; generating received light signals with a photodetector based on light received through the endoscope light pipe by the photodetector; displaying, with a display module, images based on the received light signals having a current image brightness; monitoring the received light signals for changes to the current image brightness; and adjusting a light source illuminance level, and in some embodiments a photodetector gain and exposure time, based on the current image brightness to maintain a target image brightness of the display module. In an embodiment, a brightness adjustment step size is less than a just-noticeable difference in brightness of an eye and is directly proportional to the current image brightness.

20 Claims, 4 Drawing Sheets

(51) Int. Cl.
*H04N 23/72* (2023.01)
*H04N 23/50* (2023.01)

(56) References Cited

U.S. PATENT DOCUMENTS

| | | |
|---|---|---|
| 9,737,201 B2 | 8/2017 | Avni et al. |
| 2017/0095297 A1* | 4/2017 | Richmond ......... A61B 1/00165 |
| 2020/0069163 A1* | 3/2020 | Otani .................... A61B 1/044 |

\* cited by examiner

METHOD FOR ADJUSTING AN EXPOSURE OF AN ENDOSCOPE

CROSS-REFERENCE TO RELATED APPLICATIONS

This application is a continuation of U.S. application Ser. No. 17/123,650, filed Dec. 16, 2020, which claims the benefit of U.S. Provisional Patent Application No. 62/951,716, filed Dec. 20, 2019, which are incorporated herein by reference in entirety.

TECHNICAL FIELD

This disclosure relates generally to endoscopes, and in particular but not exclusively, relates to adjusting an exposure of an endoscope.

BACKGROUND INFORMATION

Endoscopes are currently used in a wide variety of medical procedures, such as endoscopy and laparoscopy, to both illuminate and visualize internal organs of a patient. An endoscope camera feed is typically displayed on a monitor to guide a physician in conducting the procedure.

A camera technology referred to as automatic exposure or auto-exposure automatically adjusts image brightness displayed on a monitor for viewing. However, conventional auto-exposure methods have been developed and fine-tuned for capturing scenes illuminated by external sources.

Conventional auto-exposure methods, such as those typically used in consumer electronics (e.g. video cameras and phone cameras) are designed to capture natural scenes, such as those illuminated by an external light source. Given a scene, these methods adapt to the external illumination by optimizing camera controls (exposure time, aperture size and sensor gain) to capture a well-exposed video feed. Anatomical scenes present a unique set of challenges, such as reflective instruments in proximity to a camera, for which such auto-exposure methods have not been optimized and, therefore, such conventional methods demonstrate poor performance.

Such methods typically do not work well for endoscope visualization for a number of reasons. Endoscope hardware is typically different than consumer camera hardware. Endoscopes typically do not have a camera shutter and this, therefore, restricts the camera controls that can be optimized to only exposure time and sensor gain. Endoscopes typically produce and control their own illumination. The auto-exposure methods designed for consumer cameras assume some level of external illumination and cannot control its level. As such, using an auto-exposure method optimized for consumer electronics does not benefit from the ability to actively change illumination level and preserve a good signal-to-noise ratio (SNR). Auto-exposure methods in consumer cameras are not designed to deal with challenges specific to medical procedures such as a shiny reflective instrument in the scene, instruments, and anatomy very close (e.g., <30 mm) to the camera, and operating in a closed cavity with significant surface reflectance. Consumer electronics capture videos for a different use case of post-visualization where captures can be post-processed to fix any remaining brightness issues. In contrast, endoscope visualization is live typically at 60 frames per second rate. The auto-exposure method for endoscope visualization should to be able to actively optimize screen brightness.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
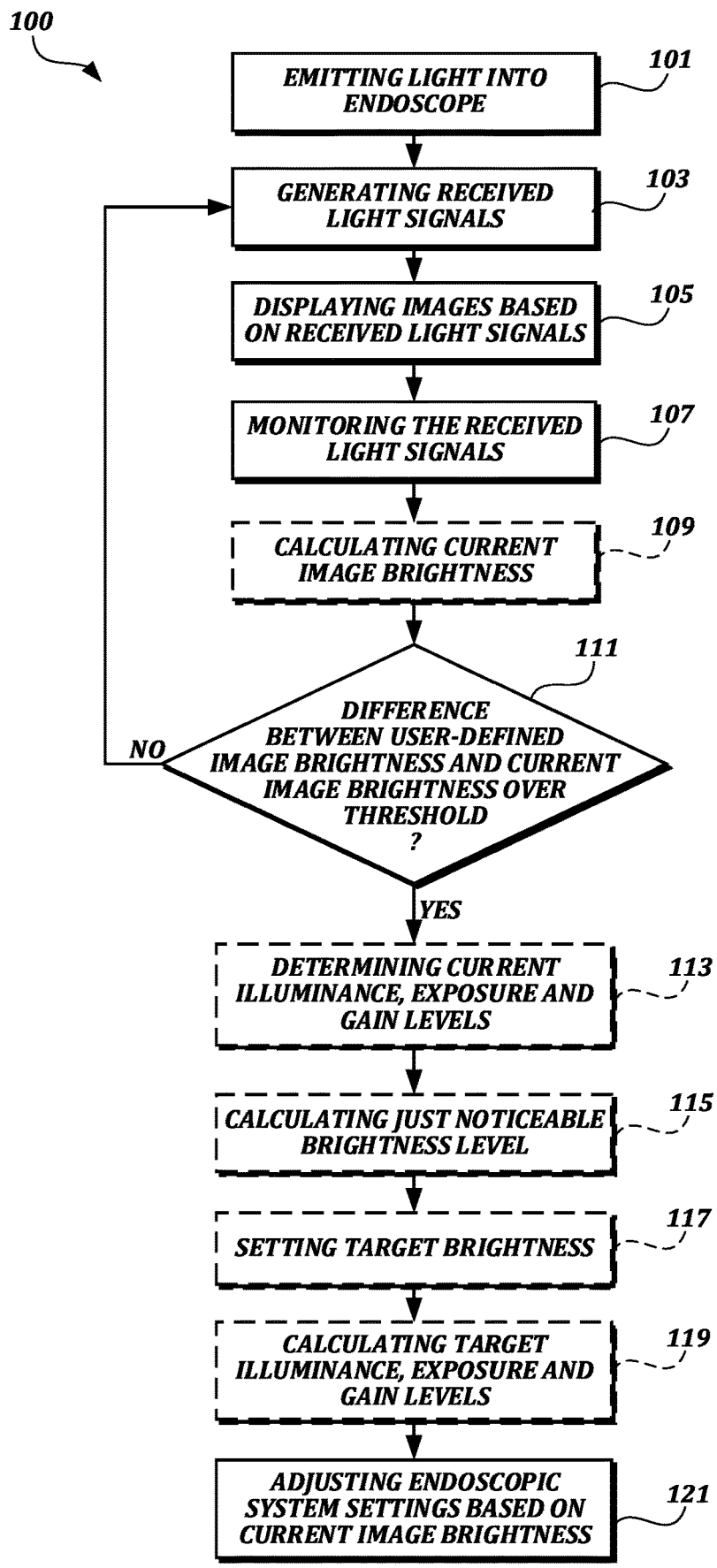
FIG. 1 is a flow chart illustrating a process of adjusting an exposure of an endoscope, in accordance with an embodiment of the disclosure.

Embodiments of methods, systems, and non-transitory, machine-readable media for adjusting an exposure of an endoscope are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The present disclosure provides methods, endoscopic systems, and non-transitory, machine-readable media for use in endoscope visualization pipelines. Typically, an endoscope not only serves as the camera, or visualization element, but also as an illumination source for a surgical scene. As such, image quality produced by an endoscope can be controlled not only by camera parameters but also by illumination parameters.

Auto-exposure methods seek to maintain a user-specified target image brightness regardless of illumination level and object reflectance. More particularly for surgical scenes, as the endoscope is moved to visualize different anatomical regions and, potentially, surgical instruments in scene, the auto-exposure method should maintain a uniform level of image brightness in video feed, such as an image brightness based upon a user input.

The methods of the present disclosure adjust an illuminance of a light source of an endoscopic system, an exposure time, and a sensor gain to maintain an even image brightness, such as while also reducing a signal-to-noise ratio (SNR), as the endoscope is moved about a surgical scene. In comparison, conventional auto-exposure methods, such as those developed for consumer video cameras, only optimize camera parameters (e.g. shutter speed, aperture size, and gain) as there is almost always some level of external illumination. Such external illumination typically cannot be controlled or measured by a camera. As a result, in dark scenes, image quality suffers from significant noise due to high exposure time and sensor gain.

In an embodiment, the methods of the present disclosure are suitable to transition between different control settings such that an image brightness change on the monitor is minimally noticeable frame-to-frame, such as to a human eye, and suitable to provide a smooth visualization experience. This is in contrast to conventional auto-exposure methods that result in scene flickering, oscillation, or flashing as a result of changing control settings. Such flickering, oscillation, or flashing adversely affects a user visualization experience because the user visualization experience is used by surgeons, for example, to guide their procedures.

A method 100, in accordance with an embodiment of the present disclosure, will now be described with respect to FIG. 1. FIG. 1 is a flow chart illustrating the method 100 of adjusting an exposure of an endoscope, in accordance with an embodiment of the disclosure.

As shown, method 100 can begin with process block 101 including emitting light into an endoscope. In an embodiment, such emission includes emitting light with a light source into a proximal end of an endoscope light pipe. At least a portion of such light is transmitted through the endoscope light pipe from the proximal end to a distal end of the endoscope light pipe, such as by total internal reflection. The portion of the light transmitted through the endoscope light pipe can be emitted from the distal end and onto a scene, such as a surgical scene inside of a body. At least a portion of the light emitted onto the scene is reflected or scattered off of the scene and again received by the distal end of the endoscope light pipe.

The light source can be any light source suitable to emit light into the endoscope light pipe. The emitted light can include light having any wavelengths suitable to interrogate a scene, such as a surgical scene. In an embodiment, the light source is configured to emit light having wavelengths in, for example, an ultraviolet range (e.g. in a range of about 10 nm to about 400 nm), a visible range (e.g. in a range of about 400 nm to about 700 nm), or an infrared range (e.g. in a range of about 700 nm to about 1 mm).

While light sources positioned at a proximal end of an endoscope light pipe are described, it will be understood that the light source can be positioned at other portions of an endoscopic system, such as at a distal end of an endoscope light pipe.

In an embodiment, process block 101 is followed by process block 103, which includes generating received light signals based on light received through the endoscope light pipe. In an embodiment, process block 103 includes generating received light signals with a photodetector based on light received through the endoscope light pipe by the photodetector, such as with a photodetector positioned at the proximal end of the endoscope light pipe. Such a photodetector may be responsive to or otherwise sensitive to light having one or more wavelengths emitted by the light source, such as in generating the received light signals. While a photodetector positioned at the proximal end of the endoscope light pipe is described, it will be understood that the photodetectors of the present disclosure can be positioned in a number of positions in an endoscopic system, in an accordance with the embodiments described herein, such as at a distal end of the endoscope light pipe.

In an embodiment, generating received light signals with a photodetector includes generating received light signals based on light received over a period of time. Such generation of received light signals can include generating a number of received light signals based on discrete periods of time. In an embodiment, generation of received light signals includes generating received light signals based on sequential discrete periods of time, such as received light signals suitable for display as a video feed of a surgical scene. In this regard, in an embodiment, the received light signals are generated at a frame rate, wherein received light signals are generated, for example, at regular intervals in sequence as time elapses.

In an embodiment, process block 103 is followed by process block 105, which includes displaying images based on the received light signals. In an embodiment, displaying images based on the received light signals includes displaying, with a display module, images based on the received light signals having a current image brightness. As discussed further herein, in an embodiment, the display module displays the images at a current image brightness based on a user-defined brightness, such as a brightness based on an input received from a user. In an embodiment, the display module displays the images as a video feed of the scene.

In an embodiment, process block 105 is followed by process block 107, which includes monitoring the received light signals. As discussed further herein, the received light signals, images, and image brightness based thereon, can change as, for example, an orientation of the distal end of the endoscope light pipe and/or a scene captured by the distal end of the endoscope light pipe change.

In an embodiment, monitoring the received light signals includes capturing a raw image generated by the photodetector, such as a current raw photodetector image. In an embodiment, monitoring the received light signals includes monitoring the received light signals for changes to the received light signals, such as changes to current image brightness, such as current image brightness of images being displayed by the display module.

In an embodiment, process block 107 is followed by process block 109, which includes calculating a current image brightness. In an embodiment, calculating a current image brightness includes calculating the current image brightness based on the received light signals. In an embodiment, process block 109 is optional. In an embodiment, a photodetector response is proportional, such as linearly proportional, to at least three factors including a light source illumination level (L), a photodetector integration or exposure time (IE), and a photodetector gain (G).

Regarding the light source illumination level, an increase in intensity/power output of the light source increases a photodetector response, such as without or without substantially adding noise to the received light signals. In an embodiment, a maximum illumination intensity is limited by patient safety, such as the safety and integrity of a portion of a body exposed the light emitted from the distal end of the endoscope light pipe. As discussed further herein in greater detail, in an embodiment, a rate of illumination intensity change is limited by any latency associated with achieving stable power output as light source intensity or power output is changed.

Regarding the exposure time, an increase in the exposure, such as a time interval used by the photodetector to capture photons, increases a photodetector response, such as without or without substantially adding noise to the received light signals. In an embodiment, a maximum integration time is limited by a frame rate of the photodetector in generating the received light signals.

Regarding gain, in an embodiment, the gain is a multiplicative factor to photodetector response. In an embodiment, an increase in the gain increases both signal and amplifies noise.

In an embodiment, current image brightness ($B_C$) can be according to Eqn. (1):

$$B_C \propto L_C \times IE_C \times G_C \qquad \text{Eqn. (1)}$$

where, $L_C$, $IE_C$ and $G_C$ represent current illumination level, current integration time, and current gain, respectively. In an embodiment, $B_C$ is calculated by performing a histogram analysis of a raw sensor image, such as while ignoring a fraction of the tail end of histogram (representing highlights) to make auto-exposure resilient to presence of, e.g., reflective surgical instruments in the scene. In an embodiment, $L_C$, $IE_C$ and $G_C$ are all endoscopic system settings that can be read directly from endoscope hardware, such as from the photodetector and the light source.

In an embodiment, method 100 includes decision block 111, which includes determining a difference between a user-defined image brightness and a current image brightness, such as a current image brightness as determined in process block 109. Such a user-defined image brightness can be an image brightness, such as from an image displayed in a display module, defined by an input from a user. As shown, if an absolute value of a difference between the user-defined image brightness and the current image brightness is over a predetermined threshold, the method 100 may continue to further process blocks described herein. As also shown, if the absolute value of difference between the user-defined image brightness and the current image brightness is under the predetermined threshold, then, in an embodiment, the method 100 may revert to process block 103 in which the photodetector generates received light signals.

In an embodiment, the predetermined threshold is suitably low to maintain the image brightness to within acceptable ranges of the user-defined image brightness as a distal end of the endoscope light pipe moves about a surgical scene. In an embodiment, the predetermined threshold is preset on the endoscopic system. In an embodiment, the predetermined threshold can be determined by a user, such as with a user interface.

In an embodiment, decision block 111 is followed by process block 113, which includes determining a current light source illuminance level, a current photodetector exposure time, and a current photodetector gain level. In an embodiment, such a determination is performed by querying one or more components of endoscopic system hardware, such as by querying the photodetector, the light source, and/or a controller operatively coupled thereto. In an embodiment, process block 113 is optional.

In an embodiment, process block 113 is followed by process block 115, which includes calculating a just-noticeable brightness difference. A just-noticeable brightness difference is a difference in image brightness that is just large enough to be detectable by an eye, such as by a human eye. As discussed further herein, it is a goal of the methods of the present disclosure to avoid flickering, oscillation, flashing, and the like in adjusting an exposure of an endoscopic system. Such flickering, oscillation, or flashing will degrade a user experience of an endoscopic system. Accordingly, as also discussed further herein, endoscopic system parameters may be adjusted, such as iteratively adjusted, in brightness adjustment step sizes less than the just-noticeable brightness difference.

In an embodiment, the just-noticeable brightness difference is calculated and/or defined according to the Weber-Fechner law, which defines the relationship between the just-noticeable difference in brightness ($dB_C$) in terms of reference brightness (B) and a constant (K), such as according to Eqn. (2):

$$dB = K \times B \qquad \text{Eqn. (2)}$$

This implies that if current brightness $B_C$ is small, smaller steps should be taken towards achieving target image brightness. Similarly, if the current brightness $B_C$ is high, larger steps can be taken towards achieving target image brightness. In an embodiment, the constant, K, depends upon image brightness, wavelengths of light of the image, and the like.

In an embodiment, process block 115 is followed by process block 117, which includes setting a target brightness. In an embodiment, target brightness can be defined according to Eqn (3):

$$B_T \propto L_T \times IE_T G_T \qquad \text{Eqn. (3)}$$

, wherein $L_T$, $IE_T$ and $G_T$ represent target light source illumination level, photodetector integration or exposure time, and photodetector gain, respectively. A goal of setting the target brightness is to find a combination of endoscopic system settings (e.g. $L_T$, $IE_T$, and $G_T$) such that target image brightness ($B_T$) can be achieved with a low or minimized SNR.

In an embodiment, setting the target brightness includes setting the target image brightness based on the user-defined image brightness. In an embodiment, process block 117 is optional. In an embodiment, the target brightness is defined according to Eqn. (4):

$$B_T = B_C + \text{sign}(B_U - B_C) \times dB_C \qquad \text{Eqn. (4)}$$

wherein $B_U$ is a user-defined image brightness.

In an embodiment, process block 117 is followed by process block 119, which includes calculating a target light source illuminance level, a target exposure time, and a target gain level. In an embodiment, such calculations are based upon the current image brightness and the target image brightness, such as may be defined in process blocks 109 and 117, respectively. In an embodiment, process block 119 is optional.

In an embodiment, process blocks 109, 113, 115, 117, or 119 can be followed by process block 121, which includes adjusting a light source illuminance level based on the current image brightness. In an embodiment, the light source illuminance level is one of a number of endoscopic system settings further including one or more of an exposure time of the photodetector and a gain of the photodetector, wherein the method includes adjusting the endoscopic system settings based on the current image brightness. Such adjustments are suitable to maintain the target image brightness of the display module, such as the received light signals change.

In an embodiment, adjusting the light source illuminance level and/or levels of other endoscopic system settings, such as a gain and an exposure time, include making brightness adjustment steps. Such brightness adjustment steps can be made iteratively. In an embodiment, the brightness adjustment step size is less than a just-noticeable difference in brightness of an eye, such that as the endoscopic system settings are changed to maintain a target image brightness within a range not noticeable to an observer view a displayed image, and the image brightness does not perceptibly change. In an embodiment, and as discussed further herein such as with respect to process block 115, such a just-noticeable difference is based on current image brightness. Accordingly, in an embodiment, the brightness adjustment size step is directly proportional to the current image brightness.

Figure 2:
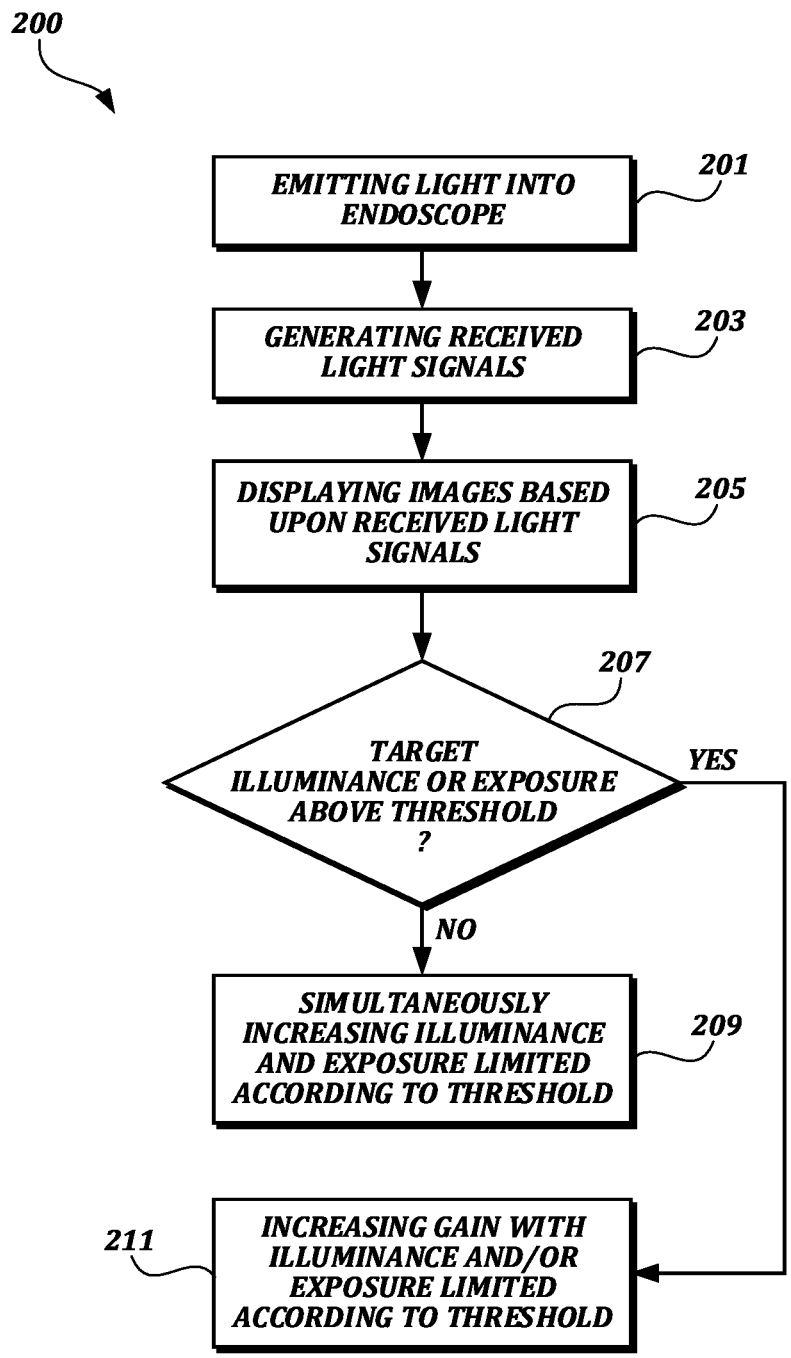
FIG. 2 is a flow chart illustrating another process of adjusting an exposure of an endoscope, in accordance with an embodiment of the disclosure.

In an embodiment, current image brightness is less than a target image brightness. Accordingly, attention is directed to FIG. 2 in which a method 200 for adjusting an exposure of an endoscopic system, according to an embodiment of the disclosure, is illustrated.

As shown, method 200 can begin with process block 201, which includes emitting light with a light source into a proximal end of an endoscope light pipe. In an embodiment, process block 201 is an example of process block 101 discussed further herein with respect to method 100 and FIG. 1.

In an embodiment, process block 201 is followed by process block 203, which includes generating received light signals. In an embodiment, generating received light signals includes generating received light signals with a photodetector based on light received through the endoscope light pipe by the photodetector positioned at the proximal end of the endoscope light pipe. In an embodiment, process block 203 is an example of process block 103 of method 100 discussed further herein with respect to FIG. 1.

In an embodiment, process 203 is followed by process block 205, which includes displaying images based upon received light signals. In an embodiment, displaying images based upon received light signals includes displaying, with a display module, images based on the received light signals having a current image brightness. In an embodiment, process block 205 is an example of process block 105 discussed further herein with respect to FIG. 1.

Figure 3:
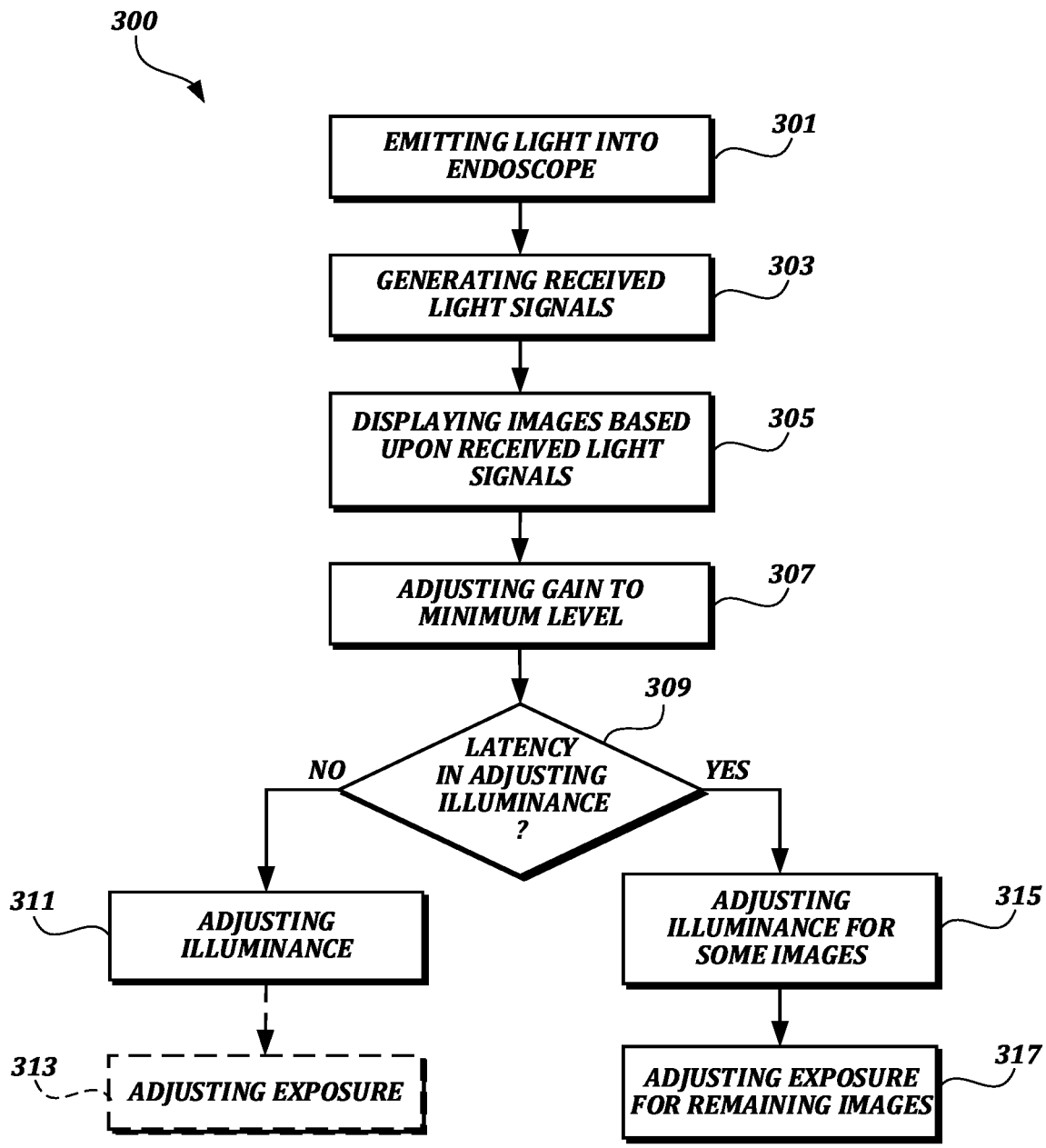
FIG. 3 is a flow chart illustrating another process of adjusting an exposure of an endoscope, in accordance with an embodiment of the disclosure.

In an embodiment, process block 205 is followed by decision block 207, which includes determining whether the target light source illuminance level and the target exposure time are limited by predetermined thresholds. In an embodiment, target image brightness, target light source illuminance level, target exposure time, target gain, and the like are calculated according to the methods described further herein with respect to methods 100 and 300 discussed further herein with respect to FIGS. 1 and 3.

In an embodiment, the target light source illuminance level is limited by patient safety. As discussed further herein, a threshold for a light source illuminance level can be limited where an illuminance level over the threshold would damage patient tissue exposed to such an illuminance level.

If the target light source illuminance level and the target exposure time are not limited by predetermined thresholds, process block 205 may be followed by process block 209, which includes increasing the light source illuminance level and the exposure time while maintaining the gain at a constant level to achieve the target image brightness. In an embodiment, increasing the light source illuminance level and the exposure time includes simultaneously increasing the light source illuminance level and the exposure time. By maintaining a photodetector gain at a constant level, such as at a minimum constant level or at a current gain level, SNR is increased or maximized. Such increasing or maximizing of SNR is suitable for producing high-quality images for display with the display module.

If the target light source illuminance level and/or the target exposure time are limited by predetermined thresholds, process block 205 can be followed by process block 211, which includes increasing the gain to achieve the target image brightness. In an embodiment, process block 211 further includes maintaining the light source illuminance level and/or the exposure time at or below the predetermined thresholds, such as to avoid damaging patient tissue.

Optimization of sensor integration time and illumination level can be done in several different ways depending on hardware properties If illumination level can be actively changed in a stable manner without disrupting video rate, illumination level can be changed first where maximum illumination is limited by patient safety and minimum illumination is limited by image noise. If BT cannot be achieved by changing illumination level, integration time is changed as a second step.

If illumination level has some latency associated with stable power output, illumination level cannot be changed in every frame. For the frames where illumination level is settling down and stabilizing, a balancing integration time change is made to keep image brightness as uniform as possible.

As discussed further herein with respect to equations 10 and 11, when $L_T$ and $IE_T$ calculated, such as with equation 9, are fractional numbers, they may be rounded off to the closest possible values. However, when $L_T$ and $IE_T$ are small values, such rounding off may result in significant overshoot or undershoot in image brightness relative to the target brightness $B_T$. To prevent this, the system checks for a brightness overshoot or undershoot. As discussed with respect to equation 10, a user-defined threshold can be used to determine whether to round up or down in adjusting the illuminance and integration time.

In an embodiment, a target image brightness is less than a current image brightness. In that regard, attention is directed to FIG. 3 in which a method 300 of adjusting an exposure of an endoscopic system, in accordance with an embodiment of the disclosure is illustrated.

As shown, method 300 begins with process block 301, which includes emitting light with a light source into a proximal end of an endoscope light pipe. In an embodiment, process block 301 is an example of process blocks 101 and/or 201 discussed further herein with respect to FIGS. 1 and 2.

In an embodiment, process block 301 is followed by process block 303, which includes generating received light signals. In an embodiment, generating received light signals includes generating received light signals with a photodetector based on light received through the endoscope light pipe by the photodetector positioned at the proximal end of the endoscope light pipe. In an embodiment, process block 303 is an example of process blocks 103 and/or 203 discussed further herein with respect to FIGS. 1 and 2, respectively.

In an embodiment, process block 303 is followed by process block 305, which includes displaying images based on the received light signals. In an embodiment, displaying images based on the received light signals includes displaying, with a display module, images based on the received light signals having a current image brightness. In an embodiment, process block 305 is an example of process blocks 105 and/or 205 discussed further herein with respect to FIGS. 1 and 2, respectively.

In an embodiment, process block 305 is followed by process block 307, which includes adjusting the gain, such as adjusting the gain to a minimum level. Using Eqns. (1) and (3), $$\frac{B_C}{B_T} = \frac{L_C \times IE_C \times G_C}{L_T \times IE_T \times G_T} \qquad \text{Eqn. (5)}$$

$$L_T \times IE_T \times G_T = L_C \times IE_C \times G_C \times \frac{B_T}{B_C} \qquad \text{Eqn. (6)}$$

Accordingly, in an embodiment, a target gain, such as a minimum target gain, is according to the Eqn. (7):

$$G_T = \text{round}\left(\frac{RHS}{IE_{Max} \times L_{Max}}\right) \text{ off to the next higher possible gain value} \qquad \text{Eqn. (7)}$$

where RHS is defined by Eqn. (8) as $$RHS = L_C \times IE_C \times G_C \times \frac{B_T}{B_C} \qquad \text{Eqn. (8)}$$

In an embodiment, adjusting the gain includes adjusting the gain to a lowest possible value, such as according to Eqns. 5-8 and where the light source illumination level and exposure time are not limited. In an embodiment, the light source illumination level is not limited by a threshold defined by a patient safety. In an embodiment, the exposure time is not limited by a frame rate of the display module.

In an embodiment, process block 307 is followed by decision block 309, which includes determining whether there is a latency in adjusting a light source illuminance level, such as in adjusting a current illuminance level to a target illuminance level. Whether a latency exists can depend on a number of factors including one or more of endoscopic device hardware including the light source, a frame rate of obtaining images, and the like.

If the light source illuminance level can be actively changed, such as from a current light source illuminance level to a target light source illuminance level, in a stable manner without disrupting video rate, light source illuminance level should be changed first where maximum illumination is limited by patient safety and minimum illumination is limited by image noise. Accordingly, in an embodiment, decision block 309 is followed by process block 311, which includes adjusting a light source illuminance level. In an embodiment, process block 311 includes adjusting the light source illuminance level such that adjusting the light source illuminance level does not affect a frame rate and accompanying exposure time of generating the received light signals with the photodetector.

In an embodiment, process block 311 is followed by process block 313, which includes adjusting the exposure time after adjusting the light source illuminance level. In an embodiment, process block 313 is optional, such as where adjusting the gain to a minimum level and adjusting the light source illuminance level is sufficient to obtain a target image brightness and/or to achieve a suitable brightness adjustment step size.

If changing the light source illuminance level has some latency associated with stable power output, a light source illuminance level is not changed in every frame. Accordingly, in an embodiment, decision block 309 is followed by process block 315, which includes adjusting the light source illuminance level on fewer than all images based on the received light signals.

In an embodiment, process block 315 is followed by process block 317, which includes adjusting the exposure time for images wherein the light source illuminance level is not adjusted. In this regard, for the frames where the light source illumination level is settling down and stabilizing, a balancing integration time change is made to keep image brightness as uniform as possible.

In an embodiment, once target gain ($G_T$) is calculated, target integration time ($IE_T$) and target illumination level ($L_T$) are simultaneously optimized:

$$L_T \times IE_T = \frac{L_C \times IE_C \times G_C \times B_T}{G_T \times B_C} \qquad \text{Eqn. (9)}$$

where, $G_T$ is the lowest sensor gain calculated in equation 7.

The simultaneous optimization of sensor integration time and illumination level can be done in several different ways depending on hardware properties If illumination level can be actively changed in a stable manner without disrupting video rate, illumination level can be changed first where maximum illumination is limited by patient safety and minimum illumination is limited by image noise. If $B_T$ cannot be achieved by changing illumination level, integration time is changed as a second step.

If illumination level has some latency associated with stable power output, illumination level cannot be changed in every frame. For the frames where illumination level is settling down and stabilizing, a balancing integration time change is made to keep image brightness as uniform as possible.

When $L_T$ and $IE_T$ calculated from equation 9 are fractional numbers, they may be rounded off to the closest possible values. However, when $L_T$ and $IE_T$ are small values, such rounding off may result in significant overshoot or undershoot in image brightness relative to the target brightness $B_T$. To prevent this, the system checks for a brightness overshoot or undershoot by calculating:

$$\left|1 - \frac{\text{round}(IE_T) \times \text{round}(L_T)}{IE_T \times L_T}\right| < \epsilon \qquad \text{Eqn. (10)}$$

where, $\epsilon$ is a user-defined threshold. If the condition is true, $IE_T$ and $L_T$ are rounded off to the closest possible values, which produces an image brightness close enough to target brightness $B_T$. However, if this condition fails, $IE_T$ and $L_T$ are floored to the next lower values and sensor gain $G_T$ is simultaneously increased to achieve the target brightness $B_T$:

$$G_T = \text{round}\left(\frac{L_C \times IE_C \times G_C \times B_T}{\text{floor}(L_T) \times \text{floor}(IE_T) \times B_C}\right) \text{ off to the closest gain value} \qquad \text{Eqn. (11)}$$

Accordingly, in an embodiment, the light source illuminance level and the exposure time are rounded up when the light source illuminance level and the exposure time are fractional numbers and a ratio of a product of a rounded light source illuminance level and a rounded exposure time to a product of a fractional light source illuminance and a fractional exposure time is below a user-defined threshold. Likewise, in an embodiment, the fractional light source illuminance and the fractional exposure time are rounded down and the gain is increased to obtain target brightness when the ratio of the product of the rounded light source illuminance level and the rounded exposure time to the product of the fractional light source illuminance and the fractional exposure time is above the user-defined threshold.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

Figure 4:
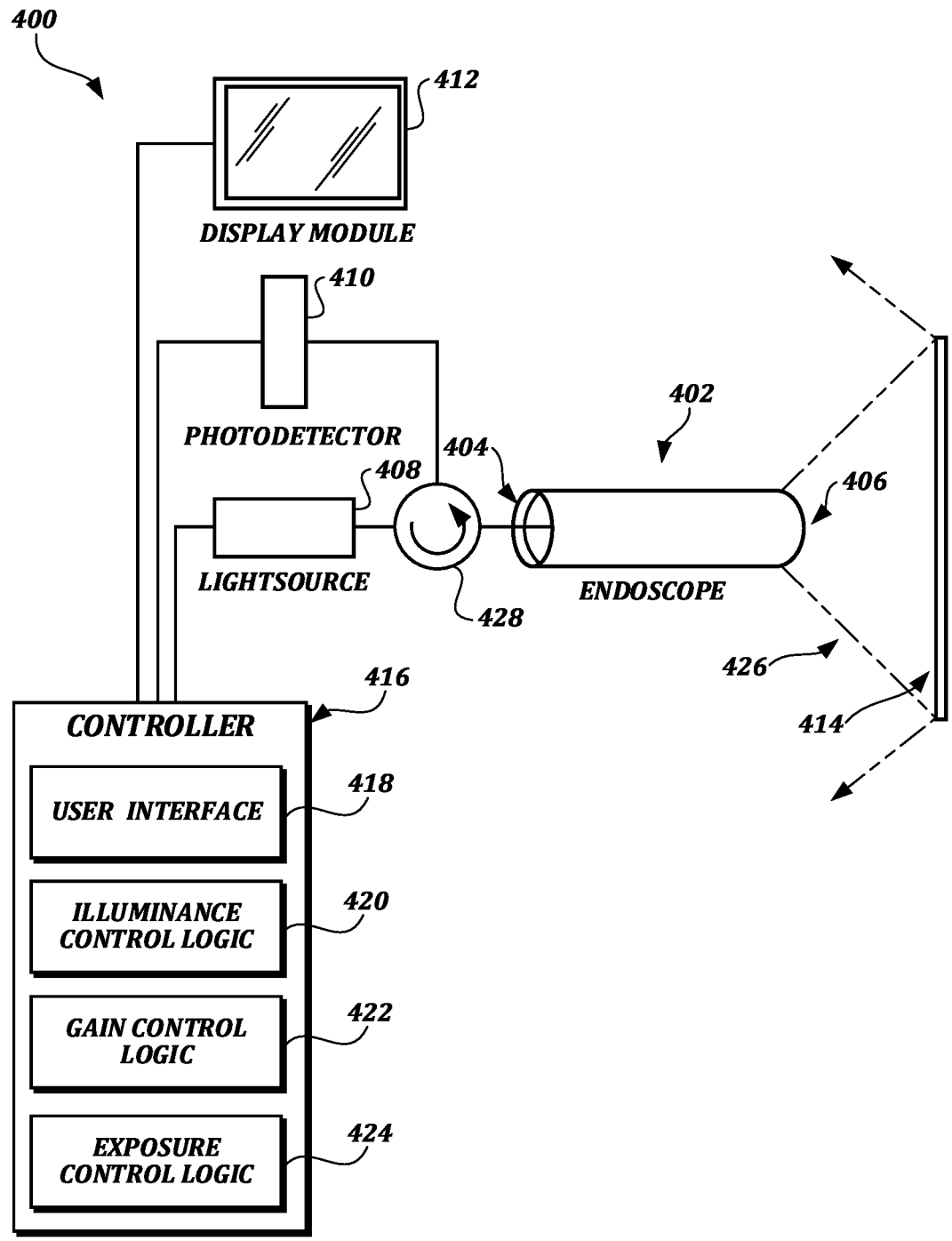
FIG. 4 a schematic illustration of an endoscopic system, in accordance with an embodiment of the disclosure.

In another aspect, the present disclosure provides an endoscopic system configured to adjust an exposure of the endoscopic system. In that regard, attention is directed to FIG. 4 in which an endoscopic system 400, in accordance with an embodiment of the disclosure, is illustrated.

As shown, the endoscopic system 400 includes an endoscope light pipe 402, a light source 408, a display module 412, and a controller 416. In the illustrated embodiment, the endoscope light pipe 402 has a proximal end 404 and a distal end 406, wherein the light source 408 positioned to emit light into the proximal end 404. In an embodiment, the endoscope light pipe 402 is flexible such that the distal end 406 can be moved about a scene 414 to receive light 426 reflected and/or scattered off of different portions of the scene 414.

The photodetector 410 is positioned to receive light 426 from the endoscope light pipe 402, such as through the proximal end 404, such as through the optical switch 428. In an embodiment, the photodetector 410 and other portions of the endoscopic system 400 do not include a shutter or other component configured to selectively occlude or limit light received from the proximal end 404 from reaching the photodetector 410. In this regard, an exposure of the endoscopic system 400 is adjusted by adjusting one or more of, for example, the light source 408 illuminance level, the photodetector 410 gain, and the photodetector 410 exposure time.

The display module 412 is shown operatively coupled to the photodetector 410 and, in this regard, is configured to display an image of a scene 414 based on light 426 received by the photodetector 410. The controller 416 is shown to be operatively coupled to the light source 408, the display module 412, and the photodetector 410. As such, the controller 416 is shown in wired communication with the light source 408, display module 412, and the photodetector 410, although wireless configurations are also within the scope of the present disclosure.

The controller 416 includes logic that, when executed by the controller 416, causes the endoscopic system 400 to perform operations. In an embodiment, such operations are suitable to perform one or more of the methods 100, 200, and 300 described further herein with respect to FIGS. 1, 2, and 3. In the illustrated embodiment, the controller 416 is shown to include illuminance control logic 420 for controlling a light source 408 illuminance level, gain control logic 422 for controlling a photodetector 410 gain level, and exposure control logic 424 for controlling a photodetector 410 gain.

In an embodiment, the controller 416 includes logic that, when executed by the controller 416, causes the endoscopic system 400 to perform operations including: emitting light 426 with the light source 408; generating received light signals with the photodetector 410 based on light 426 received by the photodetector 410 from the proximal end 404 of the endoscope light pipe 402; displaying with the display module 412 images based on the received light signals having a current image brightness; and adjusting a light source 408 illuminance level of the light source 408 based on the current image brightness to maintain a target image brightness.

In an embodiment, the light source 408 illuminance level is one of a number of endoscopic system settings configured to be adjusted to adjust an exposure of the endoscopic system 400. In an embodiment, the endoscopic system settings further include one or more of an exposure time of the photodetector 410 and a gain of the photodetector 410, wherein the operations include adjusting the endoscopic system settings based on the current image brightness. As described further herein with respect to FIGS. 1-3, such endoscopic system settings can be adjusted independently or in tandem to adjust the exposure of the endoscopic system 400.

In an embodiment, a brightness adjustment step size is less than a just-noticeable difference in brightness of an eye and is directly proportional to the current image brightness. As discussed further herein with respect to process block 115 of FIG. 1, by making brightness adjustment steps smaller than a just-noticeable difference in brightness, a target image brightness is maintained as received light signals change.

In the illustrated embodiment, the endoscopic system 400 further includes a user interface 418. In an embodiment, the user interface 418 is configured to receive an input from a user, such as an input from a user for a user-defined image brightness. In this regard, in an embodiment, the endoscopic system 400 is configured to adjust an exposure time to maintain a target image brightness based on the user-defined image brightness. In an embodiment, the controller 416 further includes logic that when executed by the controller 416 causes the endoscopic system 400 to perform operations including: calculating the current image brightness based on the received light signals; determining a current light source 408 illuminance level, a current photodetector 410 exposure time, and a current photodetector 410 gain level if a difference between the user-defined image brightness and the current image brightness is above a predetermined image brightness threshold; calculating the just-noticeable brightness difference; setting a target image brightness based on the user-defined image brightness; and calculating a target light source 408 illuminance level, a target exposure time, and a target gain level based on the current image brightness and the target image brightness.

In an embodiment, the controller 416 includes logic for adjusting the endoscopic system settings for scenarios in which the current image brightness is less than the target image brightness. In an embodiment, adjusting the endoscopic system settings include simultaneously increasing the light source 408 illuminance level and the exposure time while maintaining the gain at a constant level to achieve the target image brightness. In an embodiment, adjusting the endoscopic system settings includes increasing the gain to achieve the target image brightness, wherein the light source 408 illuminance level and the exposure time are limited by predetermined thresholds.

In an embodiment, the controller 416 includes logic for adjusting the endoscopic system settings for scenarios in which the current image brightness is greater than the target image brightness. In an embodiment, adjusting the endoscopic system settings includes adjusting the gain to a minimum level; adjusting the light source 408 illuminance level, wherein adjusting the light source 408 illuminance level does not affect a frame rate of generating the received light signals with a photodetector 410; and adjusting the exposure time after adjusting the light source 408 illuminance level. In an embodiment, adjusting the endoscopic system settings includes adjusting the gain to a minimum level; adjusting the light source 408 illuminance level on fewer than all images based on the received light signals wherein adjusting the light source 408 illuminance level has an adjustment latency; and adjusting the exposure time for images wherein the light source 408 illuminance level is not adjusted.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

In another aspect, the present disclosure provides non-transitory, machine-readable storage media having instructions stored thereon. Such instructions, when executed by a processing system, cause the processing system to perform operations, such as operations for performing one or more of the methods of the present disclosure. In an embodiment, such methods include one or more of methods 100, 200, and 300 discussed further herein with respect to FIGS. 1-3, respectively.

In an embodiment, the non-transitory, machine-readable storage medium has instructions stored thereon, which when executed by a processing system, cause the processing system to perform operations including: emitting light with a light source into a proximal end of an endoscope light pipe; generating received light signals with a photodetector based on light received through the endoscope light pipe by the photodetector positioned at the proximal end of the endoscope light pipe; displaying, with a display module, images based on the received light signals having a current image brightness; monitoring the received light signals for changes to the current image brightness; and adjusting a light source illuminance level based on the current image brightness to maintain a target image brightness of the display module.

As discussed further herein with respect to, for example, FIG. 1, the light source illuminance level is one of a number of endoscopic system settings further including one or more of an exposure time of the photodetector and a gain of the photodetector. In an embodiment, the operations include adjusting the endoscopic system settings based on the current image brightness.

In an embodiment, a brightness adjustment step size made in adjusting one or more of the endoscopic system settings is less than a just-noticeable difference in brightness of an eye and is directly proportional to the current image brightness.

In an embodiment, the non-transitory, machine-readable storage medium includes further instructions stored thereon, which when executed by a processing system, cause the processing system to perform operations to perform operations of method 100, such as discussed further herein with respect to FIG. 1, and, in particular, one or more process blocks selected from process blocks 113, 115, and 117. Accordingly, in an embodiment, the non-transitory, machine-readable storage medium includes instructions stored thereon, which when executed by a processing system, cause the processing system to perform operations comprising: calculating a current image brightness based on the received light signals; determining a current light source illuminance level, a current photodetector exposure time, and a current photodetector gain level if a difference between a user-defined image brightness and the current image brightness is above a predetermined image brightness threshold; calculating the just-noticeable brightness difference; setting a target image brightness based on the user-defined image brightness; and calculating a target light source illuminance level, a target exposure time, and a target gain level based on the current image brightness and the target image brightness.

A non-transitory, machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of adjusting an exposure of an endoscopic system, the method comprising:
    emitting light with a light source into a proximal end of an endoscope light pipe;
    generating received light signals with a photodetector based on light received through the endoscope light pipe by the photodetector;
    monitoring the received light signals for changes to a current image brightness; and
    adjusting a light source illuminance level and an exposure time of the photodetector based on the current image brightness to maintain a target image brightness
    wherein the light source illuminance level and the exposure time are rounded up when the light source illuminance level and the exposure time are fractional numbers and a ratio of a product of a rounded light source illuminance level and a rounded exposure time to a product of a fractional light source illuminance and a fractional exposure time is below a user-defined threshold, and
    wherein the fractional light source illuminance and the fractional exposure time are rounded down and a gain of the photodetector is increased to obtain a target brightness when the ratio of the product of the rounded light source illuminance level and the rounded exposure time to the product of the fractional light source illuminance and the fractional exposure time is above the user-defined threshold.

2. The method of claim 1, wherein the light source illuminance level is one of a number of endoscopic system settings further including the gain of the photodetector, wherein the method includes adjusting the endoscopic system settings based on the current image brightness.

3. The method of claim 2, wherein the current image brightness is less than the target image brightness, and wherein adjusting the endoscopic system settings comprises:
simultaneously increasing the light source illuminance level and the exposure time while maintaining the gain at a constant level to achieve the target image brightness.

4. The method of claim 2, wherein the current image brightness is less than the target image brightness, and wherein adjusting the endoscopic system settings comprises:
increasing the gain to achieve the target image brightness wherein the light source illuminance level and the exposure time are limited by predetermined thresholds.

5. The method of claim 2, wherein the current image brightness is greater than the target image brightness, wherein adjusting the endoscopic system settings comprises:
adjusting the gain to a minimum level;
adjusting the light source illuminance level, wherein adjusting the light source illuminance level does not affect a frame rate of generating the received light signals with the photodetector; and
adjusting the exposure time after adjusting the light source illuminance level.

6. The method of claim 2, wherein the current image brightness is greater than the target image brightness, wherein adjusting the endoscopic system settings comprises:
adjusting the gain to a minimum level;
adjusting the light source illuminance level on fewer than all images based on the received light signals, wherein adjusting the light source illuminance level has an adjustment latency; and
adjusting the exposure time for images wherein the light source illuminance level is not adjusted.

7. The method of claim 1, wherein a brightness adjustment step size is less than a just-noticeable difference in brightness of an eye and is directly proportional to the current image brightness.

8. The method of claim 7, further comprising:
calculating the current image brightness based on the received light signals;
determining a current light source illuminance level, a current photodetector exposure time, and a current photodetector gain level if a difference between a user-defined image brightness and the current image brightness is above a predetermined image brightness threshold;
calculating the just-noticeable brightness difference;
setting a target image brightness based on the user-defined image brightness; and
calculating a target light source illuminance level, a target exposure time, and a target gain level based on the current image brightness and the target image brightness.

9. An endoscopic system comprising:
an endoscope light pipe having a proximal end and a distal end;
a light source positioned to emit light into the proximal end;
a photodetector positioned to receive light from the endoscopic light pipe; and
a controller operatively coupled to the light source and the photodetector, the controller including logic that, when executed by the controller, causes the endoscopic system to perform operations including:
emitting light with the light source;
generating received light signals with the photodetector based on light received by the photodetector from the proximal end of the endoscope light pipe; and
adjusting a light source illuminance level of the light source and an exposure time of the photodetector based on a current image brightness to maintain a target image brightness,
wherein the light source illuminance level and the exposure time are rounded up when the light source illuminance level and the exposure time are fractional numbers and a ratio of a product of a rounded light source illuminance level and a rounded exposure time to a product of a fractional light source illuminance and a fractional exposure time is below a user-defined threshold, and
wherein the fractional light source illuminance and the fractional exposure time are rounded down and a gain of the photodetector is increased to obtain a target brightness when the ratio of the product of the rounded light source illuminance level and the rounded exposure time to the product of the fractional light source illuminance and the fractional exposure time is above the user-defined threshold.

10. The endoscopic system of claim 9, wherein the light source illuminance level is one of a number of endoscopic system settings further including the gain of the photodetector, wherein the method includes adjusting the endoscopic system settings based on the current image brightness.

11. The endoscopic system of claim 10, wherein the current image brightness is less than the target image brightness, and wherein adjusting the endoscopic system settings comprises:
simultaneously increasing the light source illuminance level and the exposure time while maintaining the gain at a constant level to achieve the target image brightness.

12. The endoscopic system of claim 10, wherein the current image brightness is less than the target image brightness, and wherein adjusting the endoscopic system settings comprises:
increasing the gain to achieve the target image brightness, wherein the light source illuminance level and the exposure time are limited by predetermined thresholds.

13. The endoscopic system of claim 10, wherein the current image brightness is greater than the target image brightness, wherein adjusting the endoscopic system settings comprises:
adjusting the gain to a minimum level;
adjusting the light source illuminance level, wherein adjusting the light source illuminance level does not affect a frame rate of generating the received light signals with a photodetector; and
adjusting the exposure time after adjusting the light source illuminance level.

14. The endoscopic system of claim 10, wherein the current image brightness is greater than the target image brightness, wherein adjusting the endoscopic system settings comprises:
adjusting the gain to a minimum level;
adjusting the light source illuminance level on fewer than all images based on the received light signals wherein adjusting the light source illuminance level has an adjustment latency; and
adjusting the exposure time for images wherein the light source illuminance level is not adjusted.

15. The endoscopic system of claim 9, wherein a brightness adjustment step size is less than a just-noticeable difference in brightness of an eye and is directly proportional to the current image brightness.

16. The endoscopic system of claim 15, wherein the controller further includes logic that when executed by the controller causes the endoscopic system to perform operations including:
calculating the current image brightness based on the received light signals;
determining a current light source illuminance level, a current photodetector exposure time, and a current photodetector gain level if a difference between a user-defined image brightness and the current image brightness is above a predetermined image brightness threshold;
calculating the just-noticeable brightness difference;
setting a target image brightness based on the user-defined image brightness; and
calculating a target light source illuminance level, a target exposure time, and a target gain level based on the current image brightness and the target image brightness.

17. A non-transitory, machine-readable storage medium having instructions stored thereon, which when executed by a processing system, cause the processing system to perform operations comprising:
emitting light with a light source into a proximal end of an endoscope light pipe;
generating received light signals with a photodetector based on light received through the endoscope light pipe by the photodetector;
monitoring the received light signals for changes to a current image brightness; and
adjusting a light source illuminance level and an exposure time of the photodetector based on the current image brightness to maintain a target image brightness
wherein the light source illuminance level and the exposure time are rounded up when the light source illuminance level and the exposure time are fractional numbers and a ratio of a product of a rounded light source illuminance level and a rounded exposure time to a product of a fractional light source illuminance and a fractional exposure time is below a user-defined threshold, and
wherein the fractional light source illuminance and the fractional exposure time are rounded down and a gain of the photodetector is increased to obtain a target brightness when the ratio of the product of the rounded light source illuminance level and the rounded exposure time to the product of the fractional light source illuminance and the fractional exposure time is above the user-defined threshold.

18. The non-transitory, machine-readable storage medium of claim 17, wherein the light source illuminance level is one of a number of endoscopic system settings further including the gain of the photodetector, and wherein the operations include adjusting the endoscopic system settings based on the current image brightness.

19. The non-transitory, machine-readable storage medium of claim 17, wherein a brightness adjustment step size is less than a just-noticeable difference in brightness of an eye and is directly proportional to the current image brightness.

20. The non-transitory, machine-readable storage medium of claim 19, further instructions stored thereon, which when executed by a processing system, cause the processing system to perform operations comprising:
calculating a current image brightness based on the received light signals;
determining a current light source illuminance level, a current photodetector exposure time, and a current photodetector gain level if a difference between a user-defined image brightness and the current image brightness is above a predetermined image brightness threshold;
calculating the just-noticeable brightness difference;
setting a target image brightness based on the user-defined image brightness; and
calculating a target light source illuminance level, a target exposure time, and a target gain level based on the current image brightness and the target image brightness.

* * * * *